(12) United States Patent
Zamfes

(10) Patent No.: US 6,389,878 B1
(45) Date of Patent: May 21, 2002

(54) GAS TRAP FOR DRILLING MUD

(76) Inventor: Konstandinos S. Zamfes, 1830-10th Avenue, S.W., Calgary (CA), T3C 0J8

( * ) Notice: Subject to any disclaimer, the term of this patent is extended or adjusted under 35 U.S.C. 154(b) by 0 days.

(21) Appl. No.: 09/559,050

(22) Filed: Apr. 27, 2000

(30) Foreign Application Priority Data

Apr. 30, 1999  (CA) ............................................. 2270833

(51) Int. Cl.⁷ ......................... G01N 33/24; G01N 7/00; G01N 1/22; E21B 47/00; B01B 19/00
(52) U.S. Cl. ...................... 73/19.09; 73/19.01; 73/19.2; 73/152.04; 96/155
(58) Field of Search ............................ 73/19.01, 19.04, 73/19.09, 19.1, 19.12, 152.04, 863.21; 96/155

(56) References Cited

U.S. PATENT DOCUMENTS

| | | | |
|---|---|---|---|
| 2,514,690 A | * | 7/1950 | Bliss et al. ................ 73/19.09 |
| 5,199,509 A | * | 4/1993 | Wright et al. ................ 175/50 |
| 5,648,608 A | * | 7/1997 | Hanson ................... 73/152.02 |
| 5,824,273 A | * | 10/1998 | Tatani et al. ................ 422/171 |

* cited by examiner

*Primary Examiner*—Hezron Williams
*Assistant Examiner*—Katina Wilson
(74) *Attorney, Agent, or Firm*—Sean W. Goodwin

(57) ABSTRACT

A gas trap liberates subterranean gases entrained in drilling muds. The trap introduces a stripping gas into a flow of mud gas for liberating mud gases. The trap comprises a pair of opposing truncated right circular vessels and having a concentric bottom mud inlet, a side mud outlet and a gas collection port in the freeboard area, at the top. A stirrer depends vertically into the trap. The stirrer has radial tubes extending from its lower end and inlet ports at its top end for forming a continuous bore and flow passage therethrough. The radial tube ends are bevelled on the trailing edge. The trap is partially immersed in mud forming a mud level in the trap and a freeboard area above containing air. When rotated, the hollow shaft spins the mud, establishing a flow through the trap and forming a turbulent low pressure area at the bevels, drawing air down the shaft from the upper ports and injecting stripping air into the mud, all of which aids in liberating gases from the mud.

20 Claims, 5 Drawing Sheets

A-A

B-B

US 6,389,878 B1

GAS TRAP FOR DRILLING MUD

FIELD OF THE INVENTION

The invention relates to apparatus and process for the extraction and collection of gases which are entrained with mud used in drilling. More particularly a vessel, a stirrer and air injection is used to assist in the liberation of gases from the mud.

BACKGROUND OF THE INVENTION

During the drilling of a subterranean well, mud is circulated downhole to carry away drill cuttings. Should gas be encountered while drilling, it becomes incorporated with the mud and is conveyed to the surface. The mud is circulated in a loop: pumped from the mud tank; downhole to the bit; up to the surface; and back to the mud tank. The gas can contain information necessary to establish whether the well has traversed a formation of interest; specifically whether hydrocarbons have been encountered.

In order to analyse the gas, it is known to insert apparatus or gas trap into the mud tank for extracting the gas. This apparatus agitates the mud so that the gas is released for collection.

More particularly, known gas traps comprise a cylindrical vessel inserted into the mud in the tank. The vessel has a transverse bottom plate formed with a bottom concentric hole. The vessel is partially submerged in the mud. Mud flows upwards into the bottom hole, establishing a mud level within the vessel.

A beater or agitator, formed like an upside down "T" or tee-bar, is rotated concentrically within the vessel, typically driven by a 1725 rpm motor. The mud spins and is thrown parabolically up the vessel's side walls. A side port in the vessel permits mud to overflow and escape the vessel when it rises up the wall. Accordingly, a flow is established, drawing fresh mud up from the bottom hole and discharging it through the side port. The agitation causes contained gas to be liberated from the incoming mud. The liberated gas is drawn from the top of the vessel and is analysed, such as by a gas detector.

As the agitator is merely a beater, the gas release is less than satisfactory.

SUMMARY OF THE INVENTION

According to the present invention, an improved gas-liberation vessel or gas trap and method of use is provided which improves the release of gases from the mud. In one embodiment, an improved stirrer rotates within the mud, causing localized reduced pressure in the mud and further injecting freeboard gases into the mud, including air and liberated gas. The freeboard gases can be recycled from the freeboard volume above the mud. As a result, an increased flow of mud gas is liberated, albeit diluted with air. A correction can be applied if concentrations are to be calculated. Additionally, the configuration of the vessel forming the trap further aids in the release of mud gas and avoids accidental entrainment of mud in the gas collection port.

More specifically, in a preferred embodiment of the present invention, the novel gas trap comprises upper and lower conical vessels joined together at their narrow truncated ends. The truncated end of the upper canister projects downwardly somewhat into the truncated end lower canister, forming a mud deflecting lip. The bottom of the trap has a mud-inlet hole. One or more mud-outlet spouts are formed partially up the side wall of the lower canister. A gas collection port is located at the top of the upper canister. A hollow rotary "T" stirrer extends vertically and concentrically into the trap. The radial extent of the "T" radial tubes have beveled outlet ports on the lee-side or trailing edge of the rotating tubes and the shaft has gas inlet ports at its upper end, above the mud, a contiguous flow passage extending therebetween. In operation, the stirrer spins and agitates the mud, lifting it inertially and parabolically up the conical side wall of the lower canister. At high mud levels (the trap is located low in the mud), or with high agitation, the mud rides high on the side walls and the lower lip prevents entry of the mud into the freeboard volume. A turbulent and low pressure area is formed at the trailing bevel outlet ports, aiding in the release of gas from the mud and drawing gas down the hollow stirrer for injection into the mud. More preferably, radial scoops are mounted to the shaft's upper inlet ports to aid in collecting freeboard air and gas. The combination of inducing low pressure in the mud and the introduction of recycled gases provides superior liberation of gas from the mud.

In a broad apparatus aspect of the invention then, a gas trap is provided comprising a vessel having a transverse circular cross-section with a concentric bottom mud inlet, a side mud outlet and a gas outlet at the top. A hollow shaft stirrer depends vertically and concentrically within the trap and has radial tubes extending from its lower end for forming a continuous bore within the shaft. The radial tube ends are bevelled on the trailing edge. Ports are formed at the top of the hollows shaft. The trap is partially immersed in mud forming a mud level in the trap and a freeboard area above containing air. When rotated, the hollow shaft spins the mud forming a turbulent low pressure area at the bevels, liberating gas from the mud and drawing air down the shaft from the upper ports and injecting air into the mud.

The above apparatus enables a novel process for the liberation of mud gases, broadly comprising the steps of: flowing mud through the vessel; agitating the flowing mud; introducing a stripping gas into the agitated and flowing mud; and collecting gas which includes mud gas liberated by the stripping gas. Preferably, the stripping gas is injected through the stirrer and more preferably the stirrer utilizes bevelled outlets for forming a low pressure in the mud.

DETAILED DESCRIPTION OF THE PREFERRED EMBODIMENT

Figures 1A, 1B:
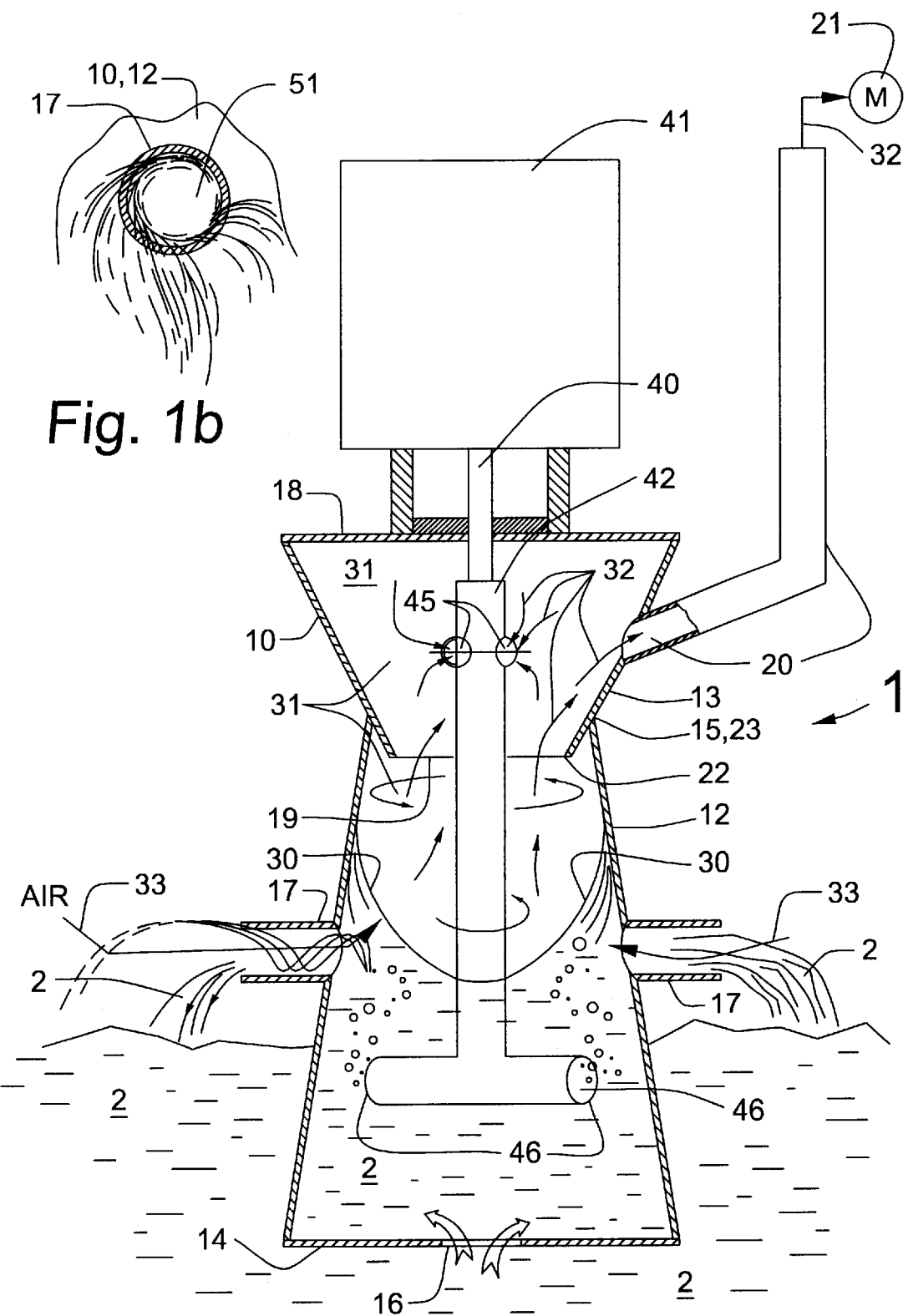
FIG. 1a illustrates a side cross-sectional view of the gas trap of one embodiment of the present invention, illustrating the upper and lower canisters with a minimum insertion into mud and a side view of the stirrer.
FIG. 1b is an end view of a side spout of FIG. 1a, illustrating the spiral flow of mud therefrom which forms an eye passage capable of admitting air into the vessel.

As shown in FIG. 1a, an improved gas-liberation gas trap comprises a vessel 1 having circular side walls 10; more particularly, upper and lower canisters 13, 12, each of which is a truncated right circular cone. The lower canister 12 is a conical vessel having a closed bottom 14 and side walls 10 which narrow upwardly. The lower canister's top end 15 is truncated and open. A centrally located mud inlet hole 16 is formed in the closed bottom 14 and one or more mud outlets or side spouts 17 are located intermediate up along the side walls 10 of the lower canister 12.

The upper canister 13 is also a conical vessel having side walls 10 which narrow downwardly. The top 18 of the upper canister 13 is closed and the bottom end 19 is truncated and open. A mud gas collection port 20 is formed adjacent the top 18 of the upper canister 13 for conducting collected gas to a meter 21 or gas detectors (not shown). Installation of an optional ball-float assembly (FIG. 2), or drain tube, aids in preventing accidental mud ingress and damage to gas detectors.

The truncated open end 19 of the upper canister 13 is smaller than the truncated open end 15 of the lower canister 12 so that it is partially insertable, and depends slightly, into the lower canister 12, forming a lower lip 22. Accordingly, in the extreme case, the lip 22 restricts inertially lifted mud 2 from entering into the upper canister 13 and deflects it downwardly. The upper and lower canisters 13, 12 are sealably joined at their connective interface 23.

The lower canister 12 is partially submerged into flowing drilling mud 2. Mud 2 enters the bottom mud inlet hole 16 and forms a mud level 30 within the lower canister 12. Above the mud level 30 is a freeboard area 31 which collects gases 32.

Gas 32 is urged out through the gas collection port 20 using sample pumps and the like, creating a slight suction in the freeboard area 31. The flow rate of the collected gas 32 is typically controlled and metered; accordingly that portion of the collected gas 32 was not liberated from the mud 2 is deemed dilution gas (typically air 33) drawn or injected into the vessel 1. Gases 32 in the freeboard area 31 result from gases being liberated from the mud 2 and from atmospheric air 33 being drawn in through the mud outlet spout or spouts 17.

A rotary shaft 40 passes downwardly through the top 18 of the upper canister 13 and is driven by a top-mounted motor 41. The shaft 40 is rotatably connected to a rotary stirrer 42 which extends downwardly into the lower canister 12.

The stirrer 42 comprises a hollow vertical shaft 43 terminated with hollow and substantially radially extending tubes 44 for forming an upside-down "T" configuration. As shown in FIGS. 1a–3 and FIG. 4, a pair of opposing inlet ports 45 are formed in the hollow shaft 43 adjacent its upper end above the mud level 30. The ends or outlet ports 46 of the radial tubes 44 are open and are bevelled in a vertical plane. A continuous passage or bore 47 is formed between the upper inlet ports 45 and the bevelled outlet ports 46 of the radial tubes 44.

Figure 2:
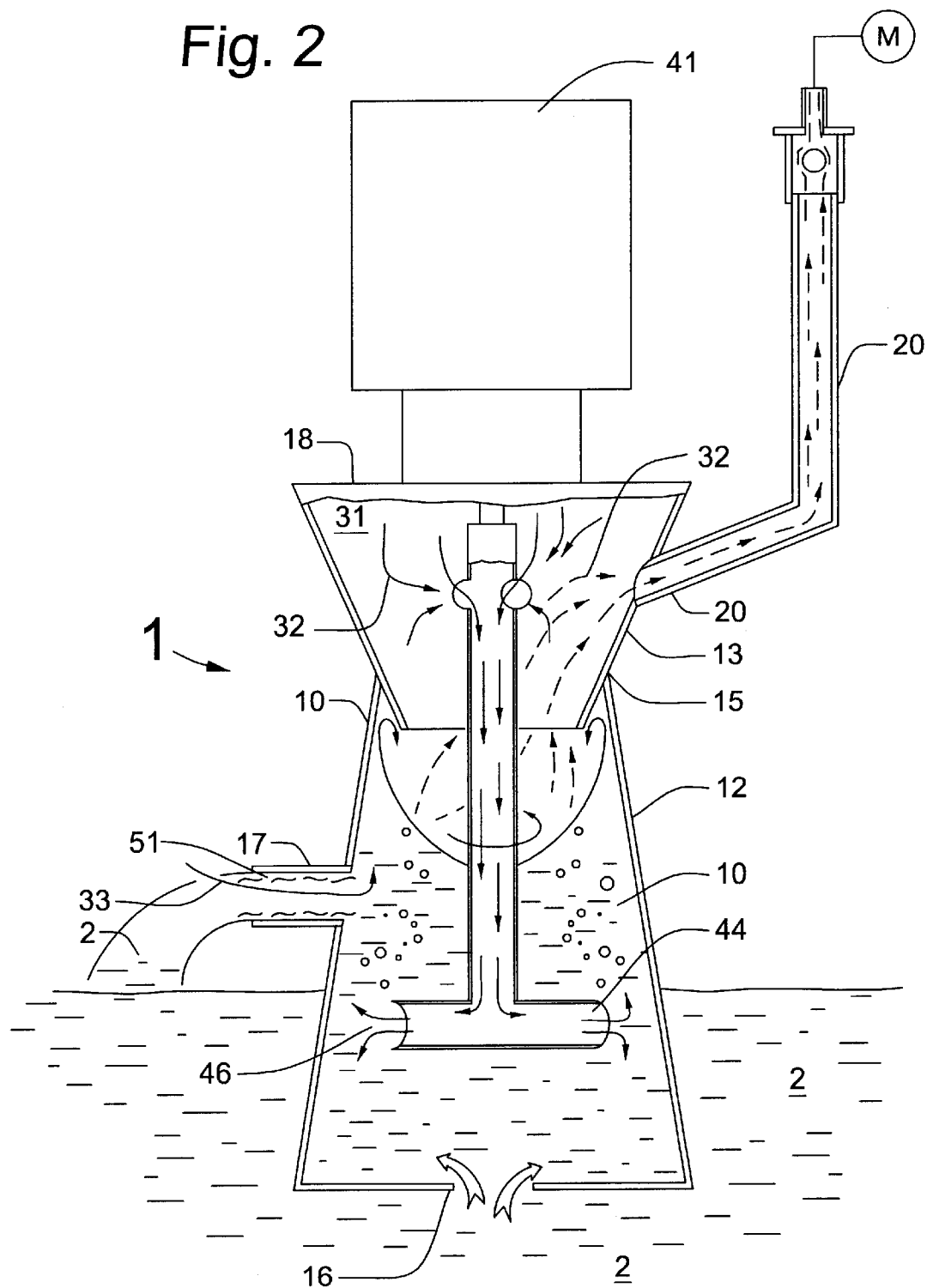
FIG. 2 is illustrates a side cross-sectional view of a gas trap and stirrer and where the trap is inserted more deeply into mud than that of FIG. 1a or the mud is more strongly agitated.
Figure 3:
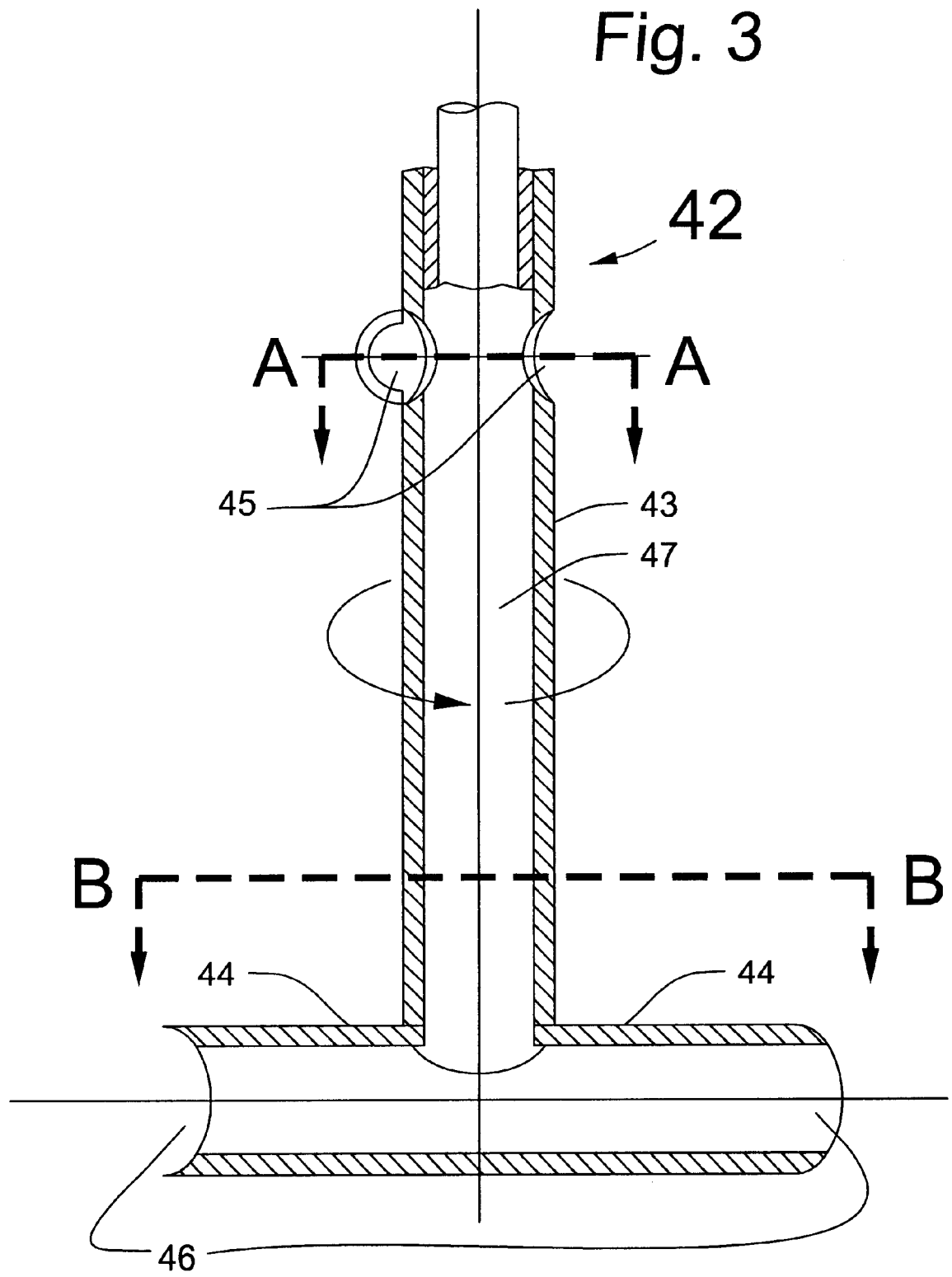
FIG. 3 is a side cross-sectional view of the hollow "T" shaft according to FIGS. 1a and 2.
Figure 4:
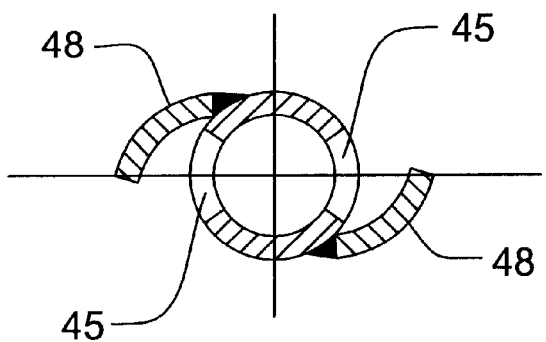
FIG. 4 is a cross-sectional view along A—A according to FIG. 3 which illustrates radial scoops.
Figure 5:
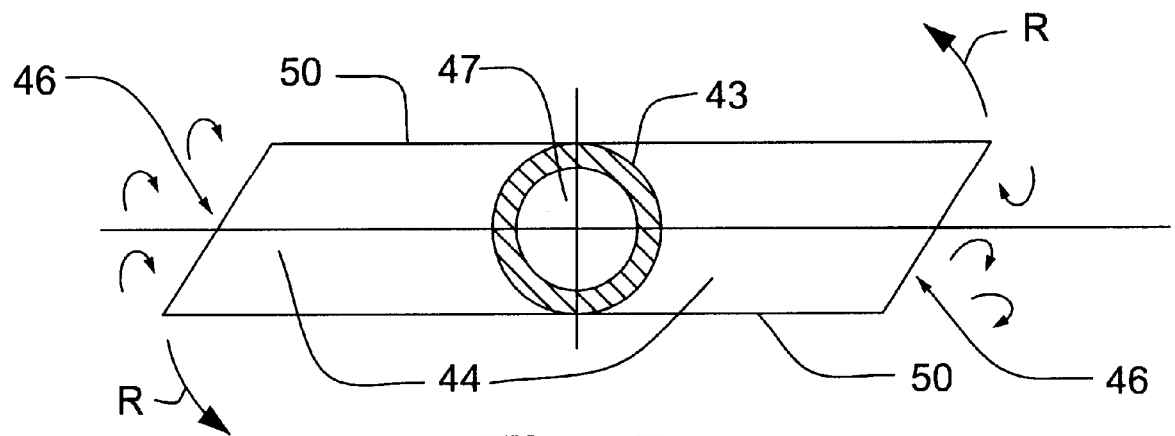
FIG. 5 is a cross-sectional view along B—B of FIG. 3 which illustrates the bevelled outlet ends.

Turning to FIGS. 3 and 5, the bevelled outlet ports 46 are shown to be formed on the lee-side or trailing edge of the radial tubes 44 as set by the normal direction of rotation; shown as counter-clockwise (CCW) in FIG. 2, as viewed from above. Simply, the bevel outlet 46 provides a rotating elliptical opening which avoids forced entry of mud 2 during stirrer rotation and further results in the formation of a low-pressure in the lee-side or wake of the rotating, bevelled outlet ports 46.

Best shown in FIG. 2, in operation, the mud is lifted inertially and parabolically up the conical wall 10 of the vessel 1. This action induces a continuous flow of mud 2 up through the bottom inlet hole 16 and out the side spouts 17. As shown in FIGS. 1a and 1b, the mud 2 spirals out from the side spouts 17, resulting in a generally central eye passage 51 therethrough which permits a countercurrent flow of air 33 in the side spouts 17 and into the vessel 1.

In cases of extreme lift, the lower lip 22 prevents entry of mud 2 into the upper canister 13 and thus avoids accidental fouling of the gas collection outlet 20.

As the stirrer 42 rotates, a low pressure area is caused at the bevel outlet ports 46, causing a turbulent decompression in the mud 2 and inducing a flow of gas 32 from the upper inlet ports 45 to the bevelled outlet ports 46, injecting stripping gases including air 33 and recycled mud gases 32 into the mud 2, and stripping or inducing liberation of gas from the mud 2. The flow of gas 32 through the shaft 43 is optionally aided by the addition of radial scoops 48 extending radially and rotationally behind each of the upper inlet ports 45.

The stripped or liberated gas and injected gases 32 rise to the freeboard area 31 for removal at the gas collection port 20.

Generally, the result of the agitation of the mud 2 with this unique stirrer 42 is the formation of a turbulent decompression at the radial ends 44 of the "T" shaft, increasing aeration of the mud 2 significantly and producing a significant improvement in the liberation of gases from the mud 2. Further, the unique design permits a much larger range of operation, continuing to process mud whether the vessel 1 is shallowly or deeply immersed in the mud 2.

Figure 6:
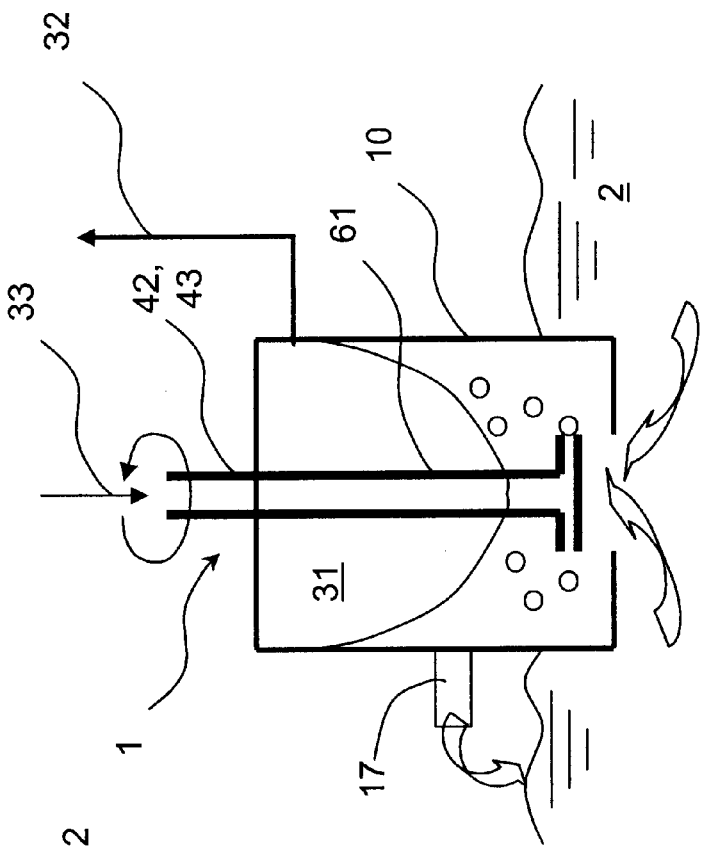
FIG. 6 is a schematic cross section of an alternate embodiment of the invention in which a sparger injects air into the agitated mud.
Figure 7:
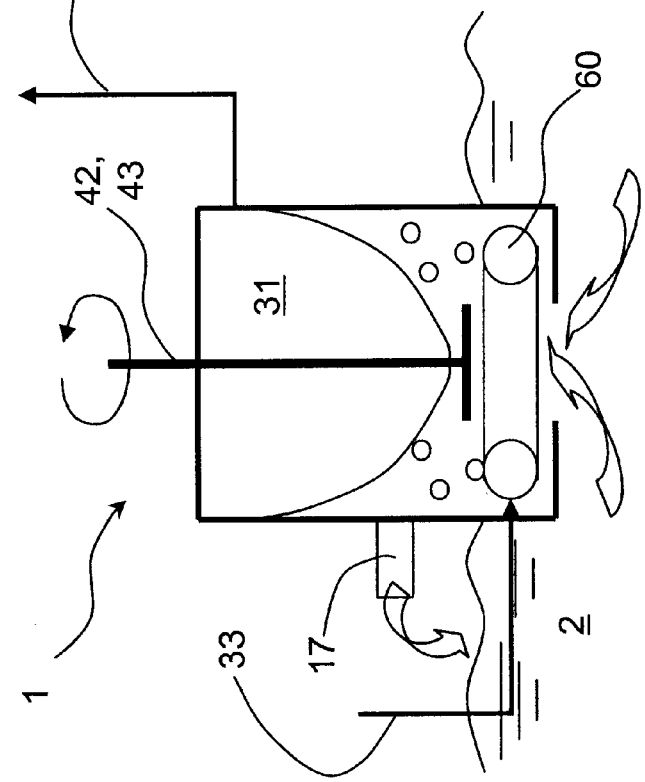
FIG. 7 is a schematic cross section of an alternate embodiment of the invention in which air is injected into mud through the stirrer.

In a less preferred, yet simpler embodiment, as shown in FIGS. 6 and 7, air 33 can be injected into the mud 2, forming bubbles in the mud 2 and liberating of mud gases 32. As shown in FIG. 6, air 33 can be injected through spargers 60. In FIG. 7, air 33 is shown being injected through the stirrer 42, the stirrer being a rotating sparger 61.

In colder operating conditions, it is advantageous to form the gas collection port 20 of upstanding metal tubing so as to best conduct and retain the residual heat of the drilling mud 2, and to further provide surface area causing entrained moisture in the collected gas 32 to condense and drain back to the vessel 1, avoiding blockages of downstream gas collection passages.

The embodiments of the invention for which an exclusive property or privilege is claimed are defined as follows:

1. A gas trap for liberating mud gas from a flow of drilling mud comprising:
    a vessel having a mud inlet immersed in the drilling mud,
        a mud outlet through which the mud is flowing, a mud level forming a freeboard volume, the freeboard volume having a mud gas collection port and a passage to the atmosphere and which contains freeboard gas which includes atmospheric air;
    means for agitating the mud in the vessel to liberate mud gas which join the freeboard gas; and
    means for recycling at least a portion of the freeboard gas into the agitated mud in the vessel so as to induce further mud gas to the freeboard gas being sampled at the collection port.

2. The trap of claim 1 wherein the agitating means comprises a rotary stirrer immersed in the mud.

3. The trap of claim 2 wherein the means for recycling freeboard gas into the mud is a sparger incorporated into the stirrer.

4. The trap of claim 3 wherein the stirrer is hollow and further comprises:

gas outlet ports formed below the mud level;

gas inlet ports formed in the freeboard volume; and a gas flow passage formed therethrough between the inlet and outlet ports for recycling freeboard gas.

5. The trap of claim 4 wherein the stirrer further comprises an axis of rotation, the outlet ports are offset from the stirrer's axis and are bevelled on a trailing edge for inducing low pressure in the mud and for inducing a recycling of freeboard gas from the stirrer's inlet ports to the outlet ports.

6. A gas trap for liberating mud gas from a flow of drilling mud comprising:

a vessel having a mud inlet adapted to be at least partially immersed in the drilling mud and a mud outlet through which the mud is flowing, a mud level forming a freeboard volume and a gas collection port in the freeboard volume; and a hollow stirrer for agitating the flowing mud and having gas inlet ports formed in the freeboard, gas outlet ports formed below the mud level and a gas flow passage formed therethrough between the inlet and outlet ports for introducing stripping gas into the flowing mud so that liberated mud gas and stripping gas is collected at the collection port.

7. The trap of claim 6 wherein the outlet ports are bevelled on their trailing edge for inducing low pressure in the mud and inducing a flow of freeboard gases from the stirrer's inlet to the outlet ports.

8. The trap of claim 7 wherein the vessel comprises a truncated cone having upwardly narrowing side walls.

9. The trap of claim 8 wherein the vessel further comprises a second upper truncated cone having downwardly narrowing side walls and a lower lip, the lower lip being fitted downwardly into the first truncated cone as a mud deflector.

10. A process for the liberation of mud gas from a flow of drilling mud comprises the steps of:

flowing mud through a vessel which has a mud level and forming a freeboard volume thereabove which contain freeboard gases;

agitating the flowing mud for liberating mud gas;

recycling a portion of the freeboard gas into the agitated and flowing mud for liberating further mud gas;

drawing freeboard gas from a collection port in the freeboard volume; and admitting atmospheric air into the freeboard volume.

11. The process of claim 10 further comprising:

rotating a hollow stirrer to agitate the mud; and recycling a portion of the freeboard gas from the freeboard volume, through the hollow stirrer and into the agitated and flowing mud.

12. The process of claim 11 further comprising:

flowing mud out of the vessel through an outlet to the atmosphere; and admitting atmospheric air through the outlet in a countercurrent flow to the flowing mud.

13. A process for the liberation of mud gas from a flow of drilling mud comprises the steps of:

flowing mud through a vessel which has a mud level forming a freeboard volume thereabove;

agitating the flowing mud by rotating a stirrer in the mud;

inducing a low pressure area in the mud using the stirrer; and introducing a stripping gas through the stirrer into the low pressure area; and collecting gas which includes mud gas liberated by the stripping gas.

14. The process of claim 13 further comprising the step of metering the collected gas for determining dilution of the mud gas.

15. A gas trap vessel for liberating mud gas from a flow of drilling mud comprising:

a lower truncated cone having upwardly narrowing side walls;

a mud inlet formed in a bottom of the truncated cone;

a mud outlet fitted in the side of the lower truncated cone and through which the mud flows and through which atmospheric air can be drawn, forming a mud level and freeboard volume thereabove for receiving liberated mud gas and containing freeboard gas which includes atmospheric air;

a gas collection port in the freeboard volume; and a rotary stirrer immersed in the flowing mud for agitating the flowing mud and liberating mud gas which combines with the freeboard gas.

16. The gas trap vessel of claim 15 further comprising an upper truncated cone having downwardly narrowing side walls and a lower lip, the lower lip being fitted downwardly into an upper end of the lower truncated cone for forming a mud deflector and wherein the collection port is located in the upper truncated cone.

17. The gas trap vessel of claim 15 further comprising means for recycling freeboard gas into the mud.

18. The gas trap vessel of claim 17 wherein the means for circulating liberated mud gas comprised a sparger incorporated into the stirrer.

19. The gas trap vessel of claim 18 wherein the stirrer is hollow and has an axis of rotation, the trap further comprising:

gas outlet ports formed below the mud level and offset from the stirrer's axis of rotation;

gas inlet ports formed in the freeboard volume; and a gas flow passage formed therethrough between the inlet and outlet ports for recycling freeboard gas.

20. The gas trap vessel of claim 19 wherein the stirrer further comprises an axis of rotation, the outlet ports are offset from the stirrer's axis and are bevelled on a trailing edge for inducing low pressure in the mud and for inducing a recycling flow of freeboard gas from the stirrer's inlet ports to the outlet ports.

* * * * *